(12) United States Patent
Lee (10) Patent No.: US 10,471,170 B2
(45) Date of Patent: Nov. 12, 2019

(54) AIR PURIFYING STERILIZER MODULE WITH IMPROVED CATALYTIC PERFORMANCE AND AIR PURIFYING STERILIZER INCLUDING THE SAME

(71) Applicant: PURESYS CO., LTD., Daejeon (KR)

(72) Inventor: Woo-Young Lee, Daejeon (KR)

(73) Assignee: PURESYS CO., LTD., Daejeon (KR)

( * ) Notice: Subject to any disclaimer, the term of this patent is extended or adjusted under 35 U.S.C. 154(b) by 298 days.

(21) Appl. No.: 15/556,707

(22) PCT Filed: Nov. 27, 2015

(86) PCT No.: PCT/KR2015/012804
§ 371 (c)(1),
(2) Date: Sep. 8, 2017

(87) PCT Pub. No.: WO2017/003046
PCT Pub. Date: Jan. 5, 2017

(65) Prior Publication Data
US 2018/0050124 A1    Feb. 22, 2018

(30) Foreign Application Priority Data

Jun. 29, 2015   (KR) .................. 10-2015-0092076

(51) Int. Cl.
*A61L 9/20* (2006.01)
*B01J 21/06* (2006.01)
(Continued)

(52) U.S. Cl.
CPC .............. *A61L 9/205* (2013.01); *A61L 9/032* (2013.01); *B01D 53/885* (2013.01); *B01J 21/06* (2013.01); *B01D 2259/804* (2013.01)

(58) Field of Classification Search
CPC ........ A61L 9/205; A61L 9/032; B01D 53/885
See application file for complete search history.

(56) References Cited

U.S. PATENT DOCUMENTS

2015/0037217 A1*  2/2015  Park ...................... F24F 3/1603
                                                        422/121

FOREIGN PATENT DOCUMENTS

KR    10-2005-0005716 A    1/2005
KR       10-0625219 B1     9/2006
(Continued)

*Primary Examiner* — Sean E Conley
(74) *Attorney, Agent, or Firm* — Rabin & Berdo, P.C.

(57) ABSTRACT

The present invention relates to an air refining and purifying sterilization module and an air refining and purifying sterilizer including the same, and more particularly, to an air refining and purifying sterilization module and an air refining and purifying sterilizer including the same with excellent sterilization, purification, deodorization, and ventilation performance with respect to various pollutants generated in smoking rooms including tobacco smoke and carbon monoxide and every living spaces as improved catalyst performance. The present invention provides an air purifying sterilizer module in which the photocatalyst unit is formed of an alloy coated metal foam carried with a photocatalytic material and an air purifying sterilizer including the same in the air purifying sterilizer module including a filter unit, a photocatalyst unit, and an ultraviolet lamp. The air purifying sterilizer module and the air purifying sterilizer including the same of the present invention can be widely used by replacing an air purifying sterilizer and an air purifier in the related art in smoke rooms, office spaces, living spaces such as apartments, hospitals, and medical facilities.

15 Claims, 8 Drawing Sheets

(51) Int. Cl.
*A61L 9/03* (2006.01)
*B01D 53/88* (2006.01)

(56) References Cited

FOREIGN PATENT DOCUMENTS

| KR | 10-1069685 B1 | 10/2011 |
| KR | 10-1419481 B1 | 7/2014 |
| KR | 10-1456116 B1 | 11/2014 |
| KR | 10-1478286 B1 | 1/2015 |
| KR | 10-2015-0048306 A | 5/2015 |
| KR | 10-2015-0062611 A | 6/2015 |

\* cited by examiner

AIR PURIFYING STERILIZER MODULE WITH IMPROVED CATALYTIC PERFORMANCE AND AIR PURIFYING STERILIZER INCLUDING THE SAME

TECHNICAL FIELD

The present invention relates to an air purifying sterilizer module and an air purifying sterilizer including the same, and more particularly, to an air purifying sterilizer module and an air purifying sterilizer including the same with excellent sterilization, purification, deodorization, and ventilation performance with respect to various pollutants generated in smoking rooms including tobacco smoke and carbon monoxide and every living spaces as improved catalytic performance.

BACKGROUND ART

Air purification sterilizers which have been used in the present are mainly configured by products for adopting a simple dust collection and deodorization type and thus smoking indoor and surrounding pollution is high. Particularly, in apartments, disputes due to inter-floor smoking problems are frequent and solutions thereof have been required, but in air purifying sterilizers in the related art, there is a limitation in catalytic performance and thus the ventilation function during smoking does not meet the demand. Particularly, carbon monoxide (CO) generated in the tobacco smoke is gas generated by incomplete combustion of carbon or a carbon-containing material and a substance that acts on the blood to reduce the ability to supply oxygen to the organism and cause suffocation, and a substance that needs to removed when an acceptable concentration of 50 ppm is exceeded, but the air purifying sterilizers in the related art do not influence a carbon monoxide removal function during smoking.

Figure 2:
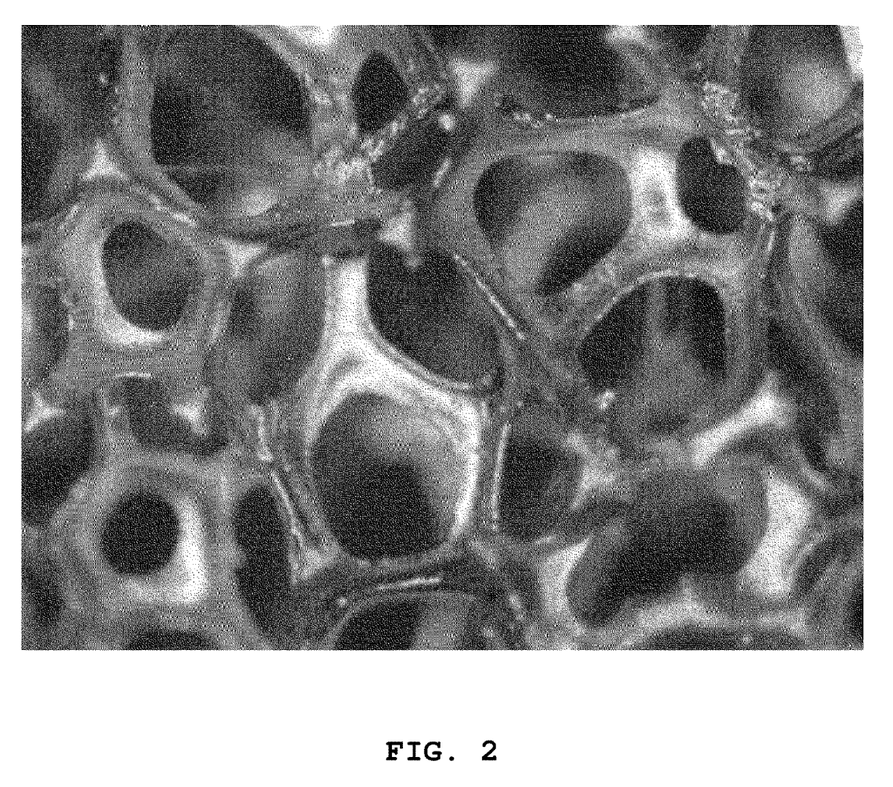
FIG. 2 is a photograph of a metal foam in the related art.

A metal foam disclosed in Korean Patent Registration No. 10-1069685 can maximize sterilization and purification by the catalyst action because a contact area is large as a porous material and has an advantage of less pressure loss due to porosity. In addition, the metal foam may have the ability to block electromagnetic waves according to an alloy material. However, in the metal foam in the related art, as illustrated in FIG. 2, it is difficult to coat the catalyst for obtaining a desired catalytic reaction because the surface is smooth and to maximize the catalytic reaction because the detachment of the catalyst frequently occurs, and performance is deteriorated over a used time and thus replacement is required, and as a result, difficulty of management and an increases in costs are caused.

PRIOR ART DOCUMENT

Patent Document

Patent Document 1: Korean Patent Registration No. 10-1419481
Patent Document 2: Korean Patent Registration No. 10-1069685
Patent Document 3: Korean Patent Registration No. 10-1478286
Patent Document 4: Korean Patent Registration No. 10-1456116

DETAILED DESCRIPTION

Technical Problem

An air purifying sterilizer is required so as to maintain pleasant indoor air by rapidly removing indoor pollutants such as tobacco smoke and carbon monoxide below an acceptable level, but in air purifying sterilizers in the related art, it is difficult to satisfy the requirement due to a limitation of catalytic performance.

An object of the present invention is to provide an air purifying sterilizer module and an air purifying sterilizer including the same having excellent ventilation and carbon monoxide removal functions by improving the catalytic performance.

Further, another object of the present invention is to provide an air purifying sterilizer module and an air purifying sterilizer including the same having excellent complex performance by combining a filter unit and other catalyst units in the catalyst unit improved by using the alloy coated metal foam.

Technical Solution

An aspect of the present invention provides an air purifying sterilizer module including:
a filter unit including a pre filter and a hepa filter;
a photocatalyst unit in which a photocatalyst is carried into an alloy coated metal foam;
a deodorizing catalyst unit in which a deodorizing catalyst is carried into the alloy coated metal foam;
an ultraviolet lamp,
wherein the alloy coated metal foam is obtained by coating a binder on a metal foam made of any one of nickel; iron; copper; and aluminum, uniformly coating alloy powder, and heating and sintering at 1,000 to 1,400° C., and a pore size is 250 μm to 2 mm, a maximum porosity is 90 to 97%, and a density is 300 g/m$^2$ to 5,000 g/m$^2$.

The alloy coated metal foam may be use a nickel foam.

The alloy powder may use all alloy powders suitable to be used as a supporter of the catalyst in addition to a metal forming the foam and preferably, may include any one of NiFeCrAl and FeCrAl.

The photocatalyst may use at least one selected from a group constituted by $TiO_2$, $Fe_2O_3$, $WO_3$, $ZnO$, and $ZrO_2$.

The photocatalyst unit may further carry at least one catalytic material selected from a group consisting of CuO, $MnO_2$, and $Al_2O_3$ into the alloy coated metal foam.

The deodorizing catalyst may use at least one selected from a group consisting of $MnO_2$, CuO, and $Al_2O_3$. More preferably, the deodorizing catalyst may use a mixture of $MnO_2$ and CuO or use $MnO_2$.

The filter unit may include a pre filter and a hepa filter.

The air purifying sterilizer module may further include a low-temperature catalyst deodorizing filter. The low-temperature deodorizing filter may include a catalytic material functioned at room temperature or below carried into an absorbent material. The low-temperature deodorizing filter may be more preferably formed in a 3D regular shape after adding and mixing a catalytic material functioned at room temperature or below and a binder in granular activated carbon, and in this case, the catalytic material may be at least one selected from a group consisting of CuO, $MnO_2$, and $Al_2O_3$.

The air purifying sterilizer module of the present invention may further include a fragrance if necessary and preferably, may include a solid ceramic natural aromatic fragrance.

In the air purifying sterilizer module of the present invention, the photocatalyst unit and the ultraviolet lamp may be alternately laminated to form a 'catalyst-lamp stacked body' and included in plural, respectively. In the air purifying sterilizer module of the present invention, the pre filter, the hepa filter, and the catalyst-lamp stacked body may be sequentially installed and included.

Another aspect of the present invention provides a method of manufacturing an air purifying sterilizer module including:

a process of preparing an alloy coated metal foam including coating a binder on a metal foam made of any one of nickel; iron; copper; and aluminum, uniformly coating alloy powder on the metal foam coated with the binder, and heating and sintering the metal foam coated with the alloy powder at 1,000 to 1,400° C.;

a process of preparing a photocatalyst unit carrying a photocatalyst in the alloy coated metal foam;

a process of preparing a deodorizing catalyst unit carrying a deodorizing catalyst in the alloy coated metal foam; and a process of manufacturing the air purifying sterilizer module by combining a filter unit including a pre filter and a hepa filter, the photocatalyst unit, the deodorizing catalyst unit, and a ultraviolet lamp.

The photocatalyst may be carried by immersing an alloy coated metal foam in a photocatalytic solution mixed with a liquefied photocatalyst and a powder photocatalyst for 30 to 60 minutes and then heating the alloy coated metal foam at 100 to 120° C. The photocatalytic solution may be used by mixing the liquefied photocatalyst and the powder photocatalyst with 2:1 to 1:2.

Yet another aspect of the present invention provides an air purifying sterilizer including the air purifying sterilizer module. The air purifying sterilizer may further include a fan.

Advantageous Effects

The air purifying sterilizer module and the air purifying sterilizer including the same of the present invention have high sterilization, purification, and deodorization as improved catalytic performance and particularly, excellent ventilation and carbon monoxide removal performance.

The alloy coated metal foam according to the present invention has a large surface area and is 3-dimensional because alloy powder is coated and fixed on the entire surface, and thus a large amount of catalytic material can be carried, and since a contact area thereof is three times larger than that of a general metal foam, improved high catalytic performance can be shown. The photocatalyst unit of the present invention carried with the photocatalytic material in the alloy coated metal foam can remove CO, $H_2$, LNG, LPG, bad odors, $CH_4$, and the like as high catalytic performance and particularly, in the case of CO, the photocatalyst unit can oxidize and remove 99.75% or more. Furthermore, the photocatalyst unit of the present invention can be semi-permanently used because the catalyst is not detached due to good adhesion of the catalyst with the alloy coated metal foam.

Further, the air purifying sterilizer module and the air purifying sterilizer including the same of the present invention have excellent complex performance by combining a filter unit and other catalyst functions in the photocatalyst unit to have excellent sterilization, purification, deodorization, and ventilation performance for various pollutants generated in smoke rooms and daily living spaces.

Further, the air purifying sterilizer module of the present invention has excellent catalytic performance and required performance which the size is decreased, and thus the air purifying sterilizer can be small-sized if necessary.

EXPLANATION OF REFERENCE NUMERALS AND SYMBOLS

10: Air purifying sterilizer module
11: Photocatalyst unit
12: Ultraviolet lamp
13: Pre filter
14: Hepa filter
15: Deodorizing catalyst unit
16: 3D low temperature catalyst filter
10a: Case
100: Air purifying sterilizer
100a: Air purifying sterilizer case

BEST MODE

Preferred embodiments of the present invention will be described in detail with reference to the accompanying drawings.

Figure 4:
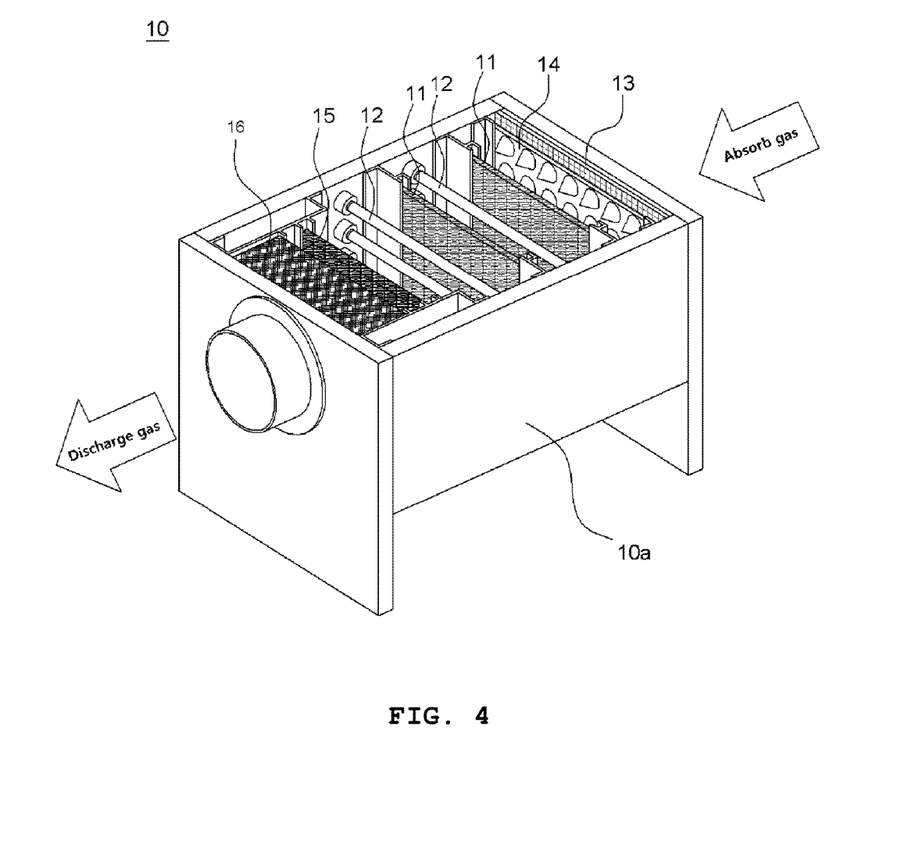
FIG. 4 is a perspective view of an air purifying sterilizer module.

An air purifying sterilizer module 10 of the present invention is illustrated in FIG. 4.

First, a configuration of a photocatalyst unit 11 and a deodorizing catalyst unit 15 configuring the air purifying sterilizer module 10 and a manufacturing method will be described. The photocatalyst unit 11 of the present invention is made of an alloy coated metal foam carried with a photocatalytic material and has a structure illustrated in a photograph of FIG. 1. The deodorizing catalyst unit 15 is also made of an alloy coated metal foam carried with a deodorizing catalyst and has substantially the same structure as the photocatalyst unit 11.

The alloy coated metal foam is prepared from a pure metal foam such as nickel, iron, copper, and aluminum and may use nickel as a preferred example.

In the case of using nickel, first, a binder is sprayed and coated on the surface of a pure nickel foam having a coil shape. This allows alloy powder to be sprayed and coated thereafter to be stably fixed onto the surface of the nickel foam, and the alloy powder is sprayed and coated after the binder is sprayed and coated. In this case, the alloy powder may use NiFeCrAl, FeCrAl, and the like. Thereafter, the alloy powder is cut in a sheet form according to a final product standard of the metal foam, transferred to a heating process, and then sintered at 1,200° C. to obtain the completed alloy coated metal foam. The heating process is a process for completing the metal foam by removing the binder material and sintering and finally, the uniform alloy coated metal foam is completed through the heating process.

Figure 1:
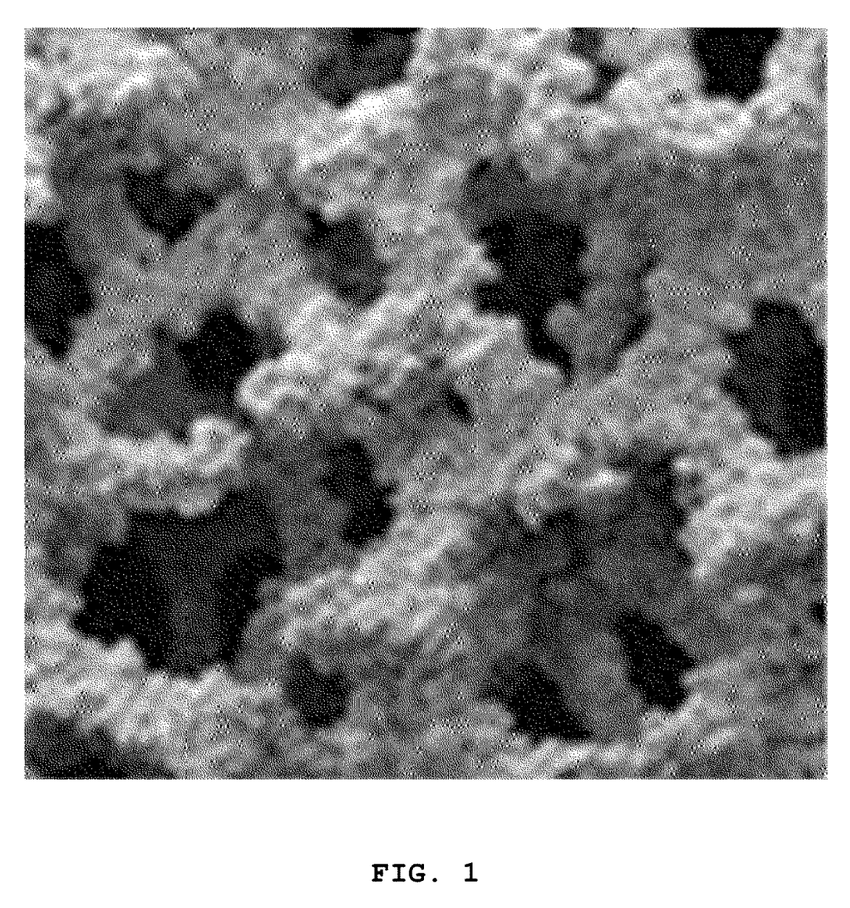
FIG. 1 is a photograph of an alloy coated metal foam according to the present invention.

The alloy coated metal foam of the present invention has a structure illustrated in FIG. 1, while the powder alloy is evenly coated and fixed on the entire surface including foam pores. Even in Korean Patent Registration No. 10-1069685 which is the prior art of the applicant of the present invention, a porous metal foam is disclosed, and in the metal foam in the related art, the surface is smooth as illustrated in FIG. 2. In the metal foam with the smooth surface, the coating of the catalyst is difficult, the removal of the catalyst frequently occurs, and the catalytic performance is deteriorated according to a use, and then the metal foam catalyst needs to be replaced. The alloy coated metal foam of the present invention is to solve the problems in the metal foam in the related art, and the alloy powder is coated on the surface of a pure metal (Ni, Fe, Cu, Al, or the like) foam through the binder and then fixed through heating and the alloy powder is uniformly and stably fixed on the entire surface including the foam pores to form a new foam surface.

The alloy coated metal foam of the present invention verified through the photograph of FIG. 1 has a large surface area which is largely extended compared with the metal foam in the related art by the alloy powder which is uniformly coated on the entire foam. Further, the alloy coated metal foam of the present invention has an excellent mechanical strength and high stability at a high temperature by heating at a high temperature and forming a stable complex with the alloy powder. The alloy coated metal foam of the present invention has a pore size of at least 250 μm to at most 2 mm. Further, the alloy coated metal foam of the present invention has a maximum porosity of 90 to 97% and generally has a porosity of at most about 95%. The density of the material may be prepared from 300 g/m$^2$ to 5,000 g/m$^2$ according to a thickness of the filter sheet. The thickness of the sheet is prepared up to 1 to 10 mm according to a porosity. The alloy coated metal foam of the present invention may carry a large amount of catalyst because an area in which the catalyst may be attached is three times larger than that of a general metal foam in the related art, and has good adhesion with the catalyst to be detached less than the general metal foam in the related art, and has high catalytic performance to be continuously used without replacement.

Figure 3:
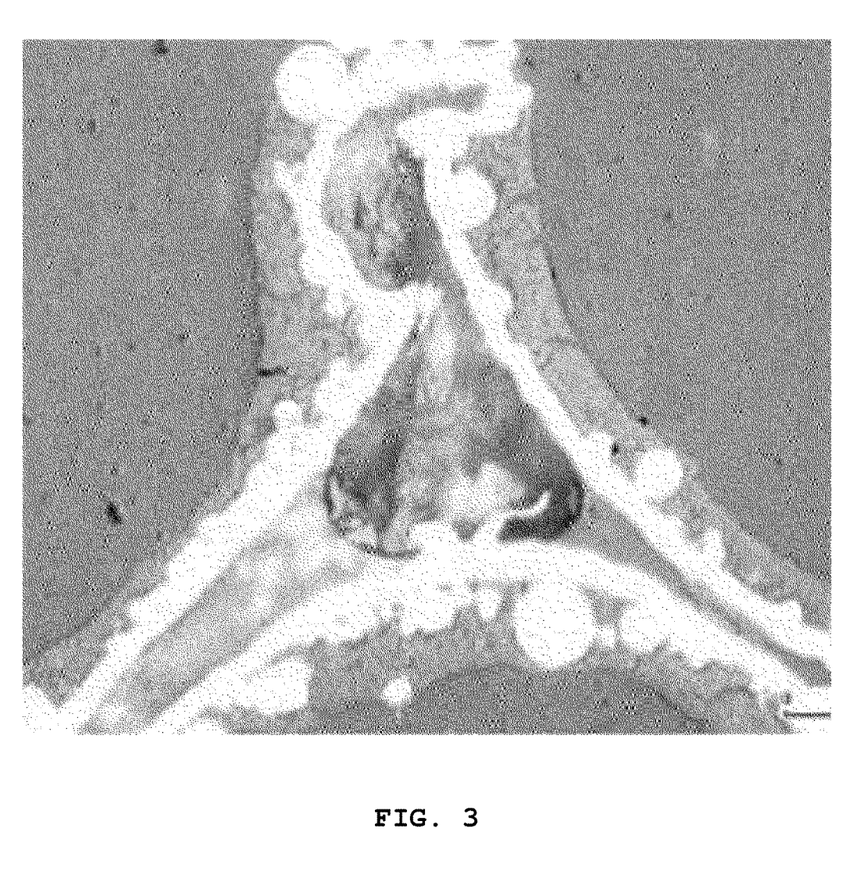
FIG. 3 is a photograph of an alloy coated metal foam carried with a catalyst.

A process of configuring the photocatalyst unit 11 by carrying the photocatalyst in the alloy coated metal foam of the present invention prepared above will be described. The photocatalytic material uses at least one selected from a group consisting of $TiO_2$, $Fe_2O_3$, $WO_3$, $ZnO$, and $ZrO_2$. Further, herein, at least one photocatalytic material selected from a group consisting of CuO, $MnO_2$, and $Al_2O_3$ may be further carried. When the carrying of the photocatalytic material is described as a preferred embodiment, the photocatalytic solution is made by mixing and stirring 50 wt % of the liquefied photocatalyst and 50 wt % of the powder photocatalyst and then the alloy coated metal foam is immersed therein for 30 to 60 minutes, heated at 110° C., and then dried. In this case, the immersing and heating processes are repeated to enhance the coating amount. FIG. 3 is a photograph of an alloy coated metal foam carried with a catalyst.

A process of configuring the deodorizing catalyst unit 15 by carrying the deodorizing catalyst in the alloy coated metal foam will be described. The deodorizing catalyst may use at least one selected from a group consisting of $MnO_2$, CuO, and $Al_2O_3$, and preferably use a mixture of $MnO_2$ and CuO or $MnO_2$. A method of carrying the deodorizing catalyst will be described as an example. A manganese dioxide catalyst is grinded with a nano size by using a jet mill and then mixed with an inorganic coupling agent and water to prepare slurry to be coated. The slurry is coated on the prepared alloy coated metal foam and dried to carry the catalyst.

In the alloy coated metal foam of the present invention, the surface is three-dimensional and the surface area is large and thus a large amount of catalytic material may be carried, and particularly, since a contact area thereof is three times larger than that of a general metal foam, more improved catalytic performance may be shown. Accordingly, the photocatalyst unit 11 and the deodorizing photocatalyst unit 15 of the present invention made of the alloy coated metal foam carried with the photocatalytic material have improved sterilization, purification, and deodorization performance and good adhesion of the catalyst with the alloy coated metal foam, and thus the catalyst is not detached and thus can be semi-permanently used. Particularly, the photocatalyst unit of the present invention may be removed by oxidizing CO, $H_2$, LNG, and LPG as improved catalytic performance, and particularly, may be removed by oxidizing 99.75% or more in the case of CO and has thermal stability up to 450° C. and has high removal efficiency for odor components and $CH_4$. Further, dusts may be operated within an available pressure loss by adjusting a cell density (alternatively, a pore density).

Figure 5:
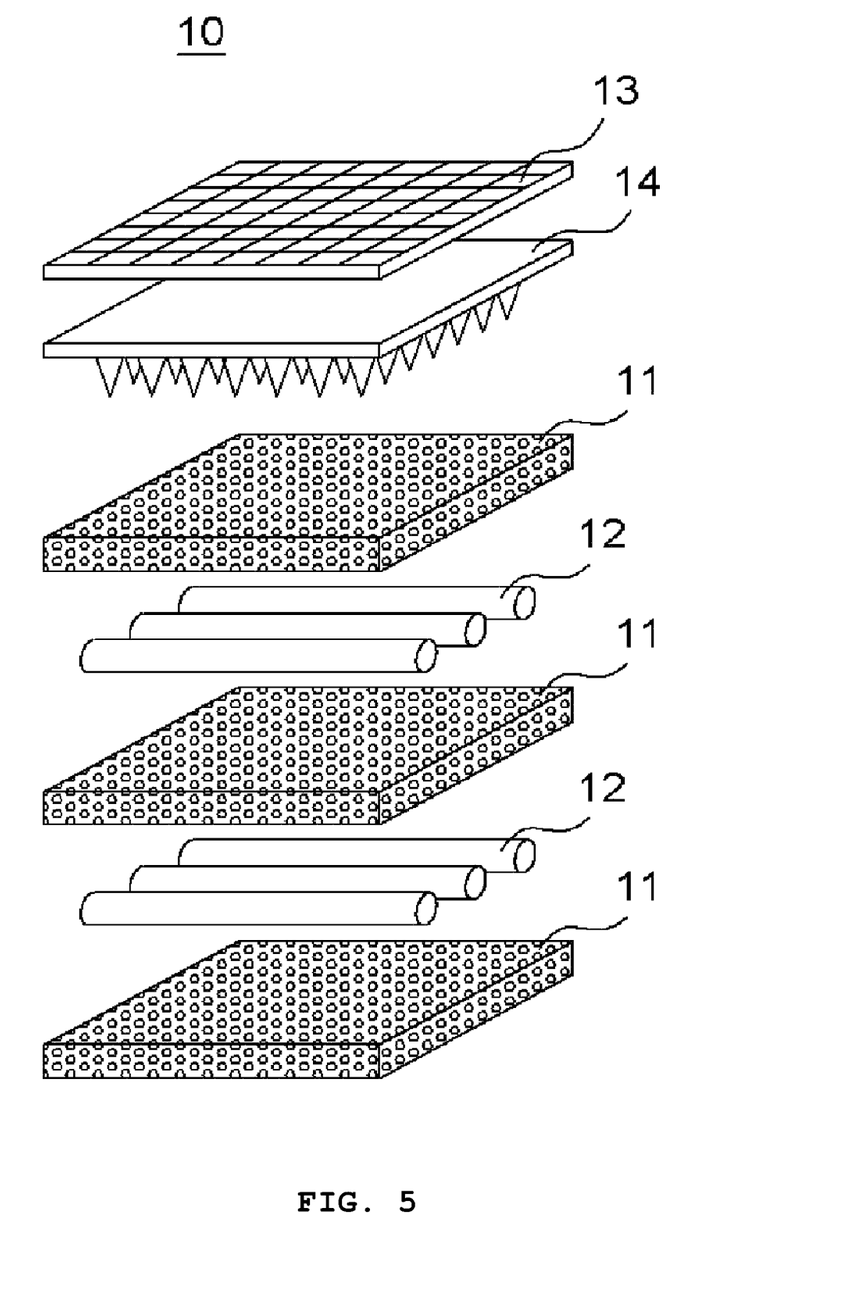
FIG. 5 is an exploded perspective view of a filter unit and a 'catalyst-lamp stacked body' in the air purifying sterilizer module.

FIG. 4 is a perspective view illustrating an air purifying sterilizer module assembled according to a preferred embodiment of the present invention and FIG. 5 is an exploded perspective view of a filter unit and a 'catalyst-lamp stacked body' configuring the air purifying sterilizer module.

The air purifying sterilizer module illustrated in FIG. 4 includes a filter unit including a pre filter 130 and a hepa filter 14; a photocatalyst unit 11 where a photocatalyst is carried in an alloy coated metal foam; a deodorizing catalyst unit 15 where a deodorizing catalyst is carried in the alloy coated metal foam; an ultraviolet lamp 12, and a low-temperature catalyst deodorizing filter 16.

The filter unit including the pre filter 13 and the hepa filter 14 may physically remove air pollutants. The pre filter 13 primarily removes large dust included in air introduced from the outside. The pre filter 13 may be a washable filter capable of reducing initial maintenance costs. The hepa filter 14 may remove pollutants having a micron size and is installed at the rear end of the pre filter 13 to secondarily remove moisture and fine dusts in the air. The hepa filter may be formed in a BAG filter. The filter unit may be installed at an entry part or a rear end of the apparatus. The more detailed contents of the pre filter and the hepa filter follow Korean Patent Registration Nos. 10-1419481 and 10-1069685 which are the prior arts of the applicant of the present invention.

In the air purifying sterilizer module of the present invention, the photocatalyst unit 11 may be included in one or in plural, and preferably, a photocatalytic reaction layer is multilayered by alternately stacking the photocatalyst unit 11 and the ultraviolet lamp 12, that is, forming the 'catalyst-lamp stacked body' in order of the photocatalyst unit 11, the ultraviolet lamp 12, the photocatalyst unit 11, the ultraviolet lamp 12, and the photocatalyst unit 11 to more increase efficiency. The ultraviolet lamp 12 is irradiated to the air passing through the photocatalyst unit by such a configuration. A plurality of ultraviolet lamps may be installed in a vertical direction to a progression direction of the air as illustrated in FIG. 5.

The air purifying sterilizer module of the present invention may further include a 3D low temperature catalyst filter 16 having both absorption performance and catalyst performance in order to increase the air purification efficiency. In the present invention, the "3D low temperature catalyst filter" is defined as a filter in which a catalytic material functioning at a low temperature and room temperature is included in activated carbon. The 3D low temperature catalyst filter 16 may be used by adding a catalyst (a catalytic material functioning at a low temperature and room temperature) and a binder to granular activated carbon and then compressive-molding the catalyst or processing the catalyst carried in a silicon mold to form a 3D shape. The activated carbon has a small particle size, a fast absorption speed, is advantageous in terms of pressure loss, and has a large absorption amount per unit volume, and is catalyzed as compared with other absorbents to maintain corrosion resistance, heat resistance, and antibiosis to extend a life time. The catalytic material functioning at the low temperature and room temperature may use $CuO$, $MnO_2$, $Al_2O_3$, and the like. In the air purifying sterilizer module of the present invention, the 3D low temperature catalyst filter may be installed at the rear end of the catalyst-lamp stacked body. However, the 3D low temperature catalyst filter is installed at the front end of the catalyst-lamp stacked body to be included in the configuration of the filter unit and a detailed installation structure may be variously modified by considering an environment to be used by the air purifying sterilizer module of the present invention.

As illustrated in FIG. 4, in the air purifying sterilizer module 10 of the present invention, the 'catalyst-lamp stacked body' in which the filter units 13 and 14, the photocatalyst unit 11, and the ultraviolet lamp 12 are alternately stacked, the deodorizing catalyst unit 15, and the 3D low temperature catalyst filter 16 may be sequentially installed from the upper end to which air is inhaled. However, an arrangement sequence and a detailed installation structure of respective elements configuring the air purifying sterilizer module may be variously modified by considering an environment to be used by the air purifying sterilizer module.

Referring to FIG. 4, a functioning process of the air purifying sterilizer module included in the air purifying sterilizer will be described. First, contaminated air containing tobacco smoke introduced from the outside sequentially passes through the pre filter 13 and the hepa filter 14 to physically remove the contaminated material. First, the pre filter 13 primarily removes large dust and subsequently, the hepa filter 14 removes micro dust having a micron size, moisture, microorganisms, and the like. Thereafter, while the air passes through the catalyst-lamp stacked body in which the photocatalyst unit 11 and the ultraviolet lamp 12 are alternately stacked, an organic material is decomposed by photochemical reaction and the remaining contaminated material is decomposed and removed. That is, while the air alternately passes through the photocatalyst unit 11 and the ultraviolet lamp 12, CO, $H_2$, LNG, LPG, $CH_4$, odor components, and the like are oxidized, decomposed, and removed. Thereafter, while the air passes through the deodorizing catalyst unit 15, the finely remaining pollutants, CO, smoke components, odor, and the like are removed.

Figure 6:
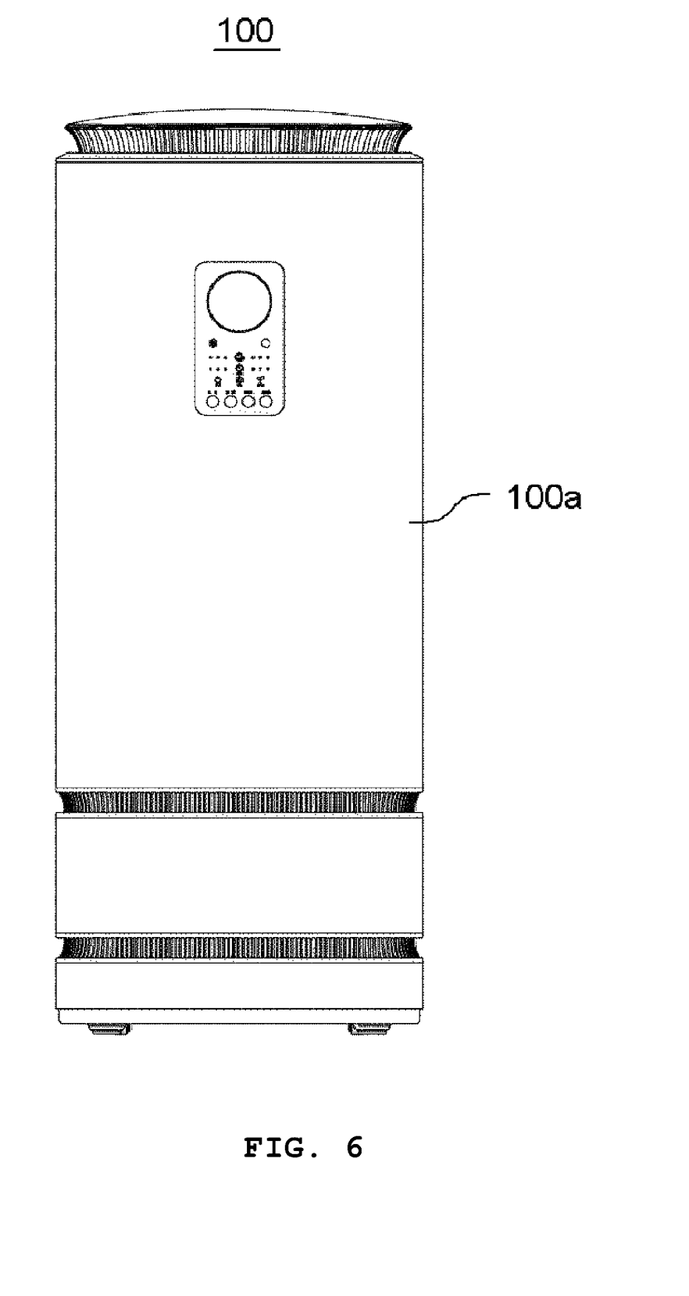
FIG. 6 is a front view of an air purifying sterilizer including the air purifying sterilizer module.

FIG. 6 is a front view of the air purifying sterilizer 100 included including the air purifying sterilizer module 10 of the present invention therein. In FIG. 6, a case 100a has a cube shape, but is not limited thereto, and a structure surface case capable of installing the air purifying sterilizer module 10 therein can have all shapes.

The air purifying sterilizer module of the present invention may be further included, and preferably, may include a solid ceramic natural aromatic fragrance (not illustrated).

In the present invention, the "solid ceramic natural aromatic fragrance" is defined as a fragrance which adjusts a fragrance amount by silicon-coating an outermost layer after aroma is absorbed through ceramic in a structure having a predetermined size formed of a ceramic material such as natural ceramics or loess.

When describing the manufacturing method, first, the ceramic material such as natural ceramics or loess is structured in a predetermined form such as ball and cubic. In this case, the size is preferably 4 to 10 mm when considering efficiency and usage, and as a preferred embodiment, the ceramic material is made with about 7 mm and installed in the air purifying sterilizer. However, the size is not particularly limited, and may be smaller or larger than 7 mm if necessary and the shape may be verified. The ceramic material is formed with predetermined shape and size such as a ball and then immersed in the natural aroma and thus the aroma is absorbed in the ceramic pores. In this case, alcohol and aldehyde which can affect the human body are not used. The silicon is coated on the surface of the ball absorbed with the aroma to adjust the fragrance amount.

When the loess is used as the ceramic material, a tourmaline component is contained into the prepared loess ball to remove bad odors, improve indoor air with far-infrared radiation, and help in anti-aging and blood circulation.

The solid ceramic natural aromatic fragrance has an effect of continuously radiating smooth and soft perfume through the silicon coating and the ceramic material such as loess is an eco-friendly material and safe even though throwing it in a flowerpot or on the ground after the perfume is exhausted.

The solid ceramic natural aromatic fragrance may be installed at a predetermined location in the air purifying sterilizer. Preferably, a plurality of solid ceramic natural aromatic fragrances may be installed at an appropriate location in the air purifying sterilizer while being contained in a permeable pouch and the like. Preferably, the solid ceramic natural aromatic fragrances are installed at the rear end of the air purifying sterilizer module where the introduced air is purified or the front end of an outlet where the purified air is discharged to maximize a fragrance effect.

The air purifying sterilizer of the present invention may include general configurations provided in a known air purifier, such as a ventilation fan, an introduction plate to which the contaminated air is introduced, and a discharge plate where the purified air is discharged. The more detailed contents of the known general configurations follow Korean Patent Registration Nos. 10-1419481 and 10-1069685 which are the prior arts of the applicant of the present invention.

Figure 7:
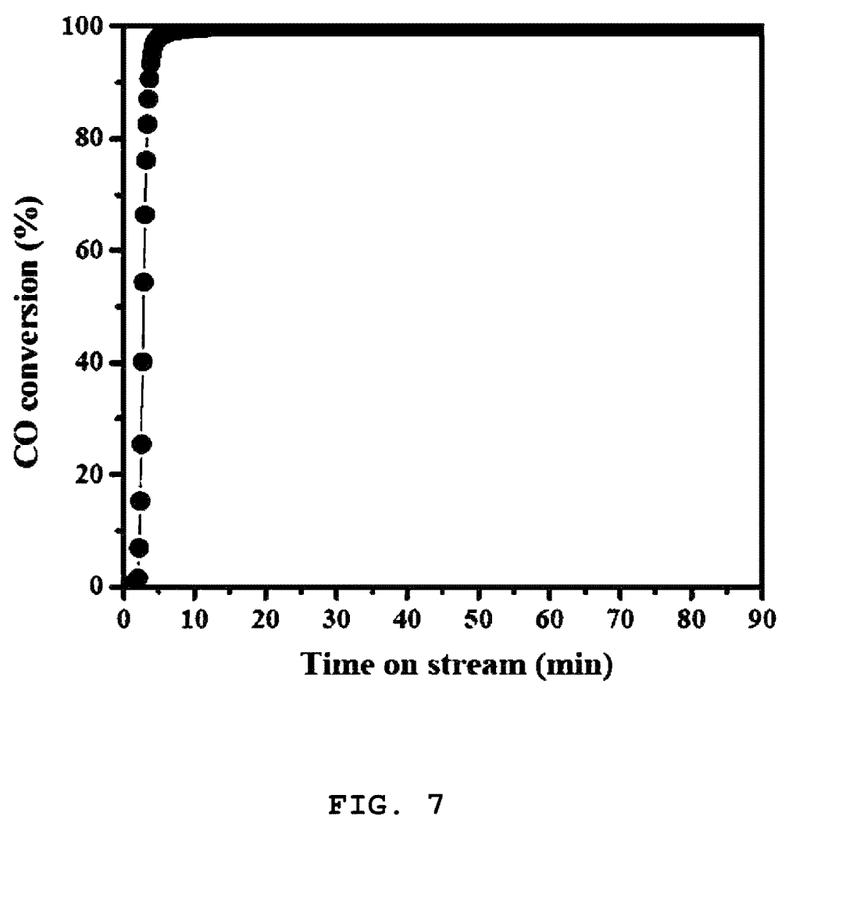
FIG. 7 is a diagram showing results of experimenting CO removal (oxidation) efficiency of the deodorizing catalyst unit carried with CuO and $MnO_2$, under a condition without moisture.
Figure 8:
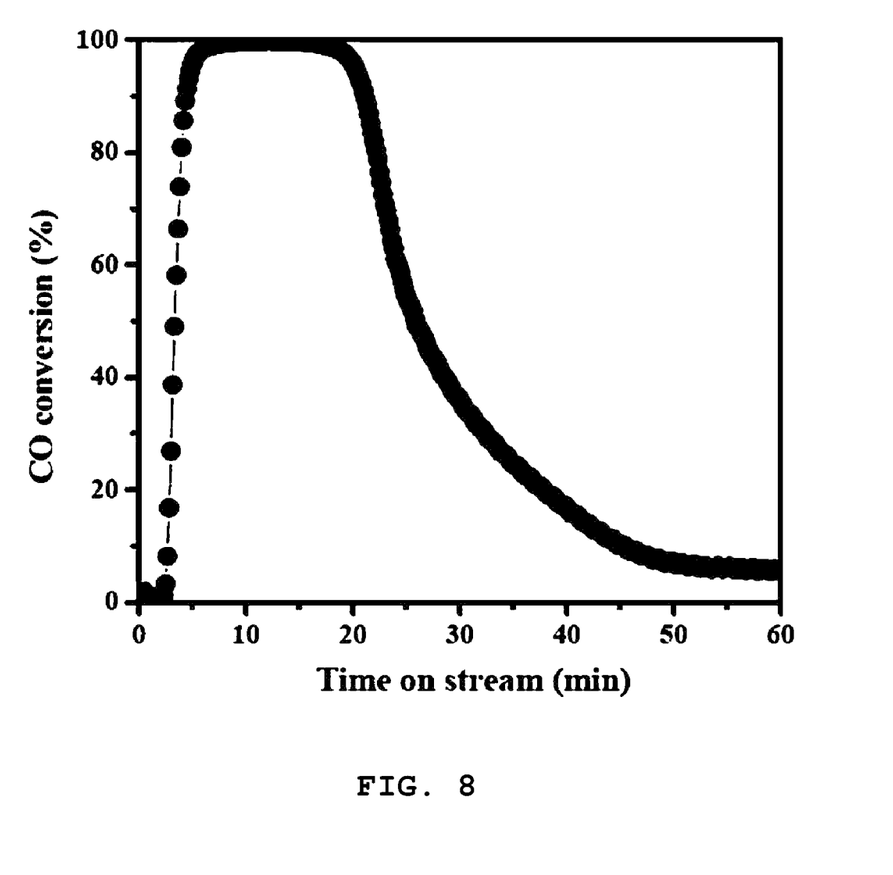
FIG. 8 is a diagram showing results of experimenting CO removal (oxidation) efficiency of the deodorizing catalyst unit carried with CuO and $MnO_2$, under a condition with moisture.

FIGS. 7 and 8 are results of experimenting CO removal (oxidization) efficiency of the deodorizing catalyst unit 15 carried with CuO and $MnO_2$. Respective experimental conditions are illustrated in Tables 1 and 2 below (in Tables, CuO and $MnO_2$ were used at 3:7). In FIG. 7, even under a condition without moisture, the CO removal efficiency was maintained for a long time. In FIG. 8, even under a condition with moisture of 1.4 wt %, the CO removal efficiency was maintained up to 20 minutes. This is a result of experimenting efficacy for the deodorizing catalyst unit 15 alone and high CO removal efficiency is shown.

TABLE 1

| Catalyst supporter | Puresys alloy coated metal foam |
|---|---|
| Catalyst | CuO, MnO$_2$ |
| Catalyst amount | Powder (45 to 106 μm) 1 g |
| Pore size | 250 μm to 2 mm |
| Contact area | 7,000 to 13,000 m$^2$/m$^3$ |
| Flow rate (SCCM) | 300 |
| WHSV (h$^{-1}$) | 18,000 |
| Temperature (° C.) | 25 |
| CO concentration (ppmv) | 2,500 |
| Absolute humidity (wt %) | 0 |

TABLE 2

| Catalyst supporter | Puresys alloy coated metal foam |
|---|---|
| Catalyst | CuO, MnO$_2$ |
| Catalyst amount | Powder (45 to 106 μm) 1 g |
| Pore size | 250 μm to 2 mm |
| Contact area | 7,000 to 13,000 m$^2$/m$^3$ |
| Flow rate (SCCM) | 300 |
| WHSV (h$^{-1}$) | 18,000 |
| Temperature (° C.) | 25 |
| CO concentration (ppmv) | 2,500 |
| Absolute humidity (wt %) | 1.4 |

The terms used in the present invention select terms used generally in the art, but are terms of meanings randomly defined by the applicant in the case of a specific case, and in this case, the terms are disclosed in the detailed description of the present invention other than general meanings of simple terms or the meanings need to be determined by considering the meanings used throughout the specification.

INDUSTRIAL AVAILABILITY

The air purifying sterilizer module and the air purifying sterilizer including the same of the present invention have excellent Sterilization, purification, deodorization, and ventilation performance for tobacco smoke and various pollutants generated in smoke rooms and daily living spaces including carbon monoxide as improved catalyst performance and thus may be widely used by replacing an air purifying sterilizer and an air purifier in the related art in smoke rooms, office spaces, living spaces such as apartments, hospitals, and medical facilities. Further, the alloy coated metal foam carried with the photocatalyst included in the air purifying sterilizer module of the present invention can be semi-permanently used because the catalyst is not detached, and thus the air purifying sterilizer of the present invention can be conveniently used in various fields as an apparatus in which catalyst replacement and management are not required.

What is claimed is:

1. An air purifying sterilizer module, comprising: a filter unit including a pre filter and a hepa filter;
   a photocatalyst unit in which a photocatalyst is carried into an alloy coated metal foam;
   a deodorizing catalyst unit in which a deodorizing catalyst is carried into the alloy coated metal foam; and
   a ultraviolet lamp,
   wherein the alloy coated metal foam is obtained by coating a binder on a metal foam made of any one of nickel; iron; copper; and aluminum, uniformly coating alloy powder, and heating and sintering at 1,000 to 1,400° C., and a pore size is 250 μm to 2 mm, a maximum porosity is 90 to 97%, and a density is 300 g/m$^2$ to 5,000 g/m$^2$.

2. The air purifying sterilizer module of claim 1, wherein the alloy powder is at least one of NiFeCrAl and FeCrAl and has a nano-sized particle diameter.

3. The air purifying sterilizer module of claim 1, wherein the photocatalyst unit further carries at least one catalytic material selected from a group consisting of CuO, MnO$_2$, and Al$_2$O$_3$ into the alloy coated metal foam.

4. The air purifying sterilizer module of claim 1, further comprising:
   a low-temperature catalyst deodorizing filter.

5. The air purifying sterilizer module of claim 1, wherein the photocatalyst is at least one selected from a group consisting of TiO$_2$, Fe$_2$O$_3$, WO$_3$, ZnO, and ZrO$_2$.

6. The air purifying sterilizer module of claim 1, wherein the deodorizing catalyst is at least one selected from a group consisting of MnO$_2$, CuO, and Al$_2$O$_3$.

7. The air purifying sterilizer module of claim 1, wherein the photocatalyst unit and the ultraviolet lamp are alternately laminated to form a catalyst-lamp stacked body and included in plural, respectively.

8. The air purifying sterilizer module of claim 4, wherein the low-temperature deodorizing filter includes a catalytic material functioned at room temperature or below carried into an absorbent material.

9. The air purifying sterilizer module of claim 4, wherein the low-temperature deodorizing filter is formed in a 3D regular shape after adding and mixing a catalytic material functioning at room temperature or below and a binder in granular activated carbon.

10. The air purifying sterilizer module of claim 8, wherein the catalytic material is at least one selected from a group consisting of CuO, MnO$_2$, and Al$_2$O$_3$.

11. The air purifying sterilizer module of claim 1, further comprising: a solid ceramic natural aromatic fragrance.

12. A method of manufacturing an air purifying sterilizer module, comprising:
   a process of preparing an alloy coated metal foam including coating a binder on a metal foam made of any one of nickel; iron; copper; and aluminum, uniformly coating alloy powder on the metal foam coated with the binder, and heating and sintering the metal foam coated with the alloy powder at 1,000 to 1,400° C.;
   a process of preparing a photocatalyst unit carrying a photocatalyst in the alloy coated metal foam;
   a process of preparing a deodorizing catalyst unit carrying a deodorizing catalyst in the alloy coated metal foam; and
   a process of manufacturing the air purifying sterilizer module by combining a filter unit including a pre filter and a hepa filter, the photocatalyst unit, the deodorizing catalyst unit, and a ultraviolet lamp.

13. The method of manufacturing an air purifying sterilizer module of claim 12, wherein the photocatalyst is carried by immersing an alloy coated metal foam in a photocatalytic solution mixed with a liquefied photocatalyst and a powder photocatalyst for 30 to 60 minutes and then heating the alloy coated metal foam at 100 to 120° C.

14. An air purifying sterilizer including the air purifying sterilizer module of claim 1.

15. The air purifying sterilizer of claim 14, further comprising:
   a fan.

* * * * *